United States Patent [19]

Bader, deceased

[11] 3,975,522

[45] Aug. 17, 1976

[54] CONTROL OF INSECTS AND ACARIDS WITH N-PHOSPHINYLAMIDINES

[75] Inventor: Jörg Bader, deceased, late of Arlesheim, Switzerland, by Dagmar Bader-Ludwig, legal representative

[73] Assignee: Ciba-Geigy Corporation, Ardsley, N.Y.

[22] Filed: July 23, 1975

[21] Appl. No.: 598,449

Related U.S. Application Data

[62] Division of Ser. No. 315,273, Dec. 14, 1972.

[30] Foreign Application Priority Data

Dec. 17, 1971  Switzerland.................. 18553/71
Feb. 19, 1972  Switzerland.................. 1869/72

[52] U.S. Cl.................. 424/200; 260/293.85; 260/945; 424/211; 424/DIG. 8
[51] Int. Cl.².................. A01N 9/36
[58] Field of Search.............. 424/200, 211, DIG. 8

[56] References Cited
UNITED STATES PATENTS

| | | | |
|---|---|---|---|
| 2,151,380 | 3/1939 | Flint et al. | 260/461 |
| 2,587,549 | 2/1952 | Trementozzi | 260/45.9 |
| 3,646,134 | 2/1972 | Hunger et al. | 260/551 P |
| 3,801,679 | 4/1974 | Hoffman et al. | 260/945 |

FOREIGN PATENTS OR APPLICATIONS

| | | |
|---|---|---|
| 2,073,668 | 10/1971 | France |
| 2,118,469 | 10/1972 | Germany |
| 1,249,343 | 10/1971 | United Kingdom |

*Primary Examiner*—Jerome D. Goldberg
*Assistant Examiner*—Allen J. Robinson
*Attorney, Agent, or Firm*—Frederick H. Rabin

[57] ABSTRACT

N-phosphinyl- or phosphinothioyl-amidines of the formula

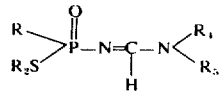

wherein
 $R_1$ represents methoxy or ethoxy
 $R_2$ represents methyl, ethyl, propyl, n-pentyl, n-hexyl, allyl or propargyl each of
 $R_4$ and $R_5$ represents allyl or
 $R_4$ and $R_5$ form, with the nitrogen atom to which they are bound, the piperidino, ring, processes for their manufacture and their use for pest control.

5 Claims, No Drawings

CONTROL OF INSECTS AND ACARIDS WITH N-PHOSPHINYLAMIDINES

This is a division of application Ser. No. 315,273, filed on Dec. 14, 1972.

The present invention relates to N-phosphinyl- or phosphinothioyl-amidines, to processes for their production, and to their use for pest control.

The amidines correspond to the formula

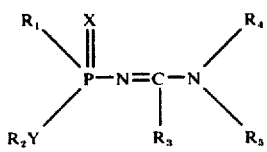

wherein
$R_1$ represents $C_1$–$C_4$-alkyl, $C_1$–$C_4$-alkylthio or $C_1$–$C_4$-alkoxy,
$R_2$ represents $C_1$–$C_7$-alkyl, propenyl or propinyl,
$R_3$ represents hydrogen, methyl or ethyl,
$R_4$ represents $C_1$–$C_6$-alkyl, $C_2$–$C_6$-alkenyl, (cycloalkyl)methyl, furfuryl or tetrahydrofurfuryl,
$R_5$ represents $C_1$–$C_6$-alkyl or $C_2$–$C_6$-alkenyl,
X and Y each represent oxygen or sulphur, or
$R_4$ and $R_5$ form, with the nitrogen atom to which they are bound, the morpholino, piperidino, methylpiperidino, pyrrolidino or hexamethyleneimino ring, or
$R_3$ with $R_4$ or $R_5$ forms a 5 or 6-membered ring, whereby the group $R_4$ or $R_5$ not participating in the ring formation then denote methyl or ethyl.

The alkyl, alkenyl and alkoxy groups concerned in the case of formula I can be branched or straight-chain. Examples of such groups are, inter alia: methyl, ethyl, isopropyl, propyl, n-, i-, sec.-, tert.-butyl, methoxy, methylthio, ethoxy, ethylthio, isopropoxy, propoxy, propylthio, n-butoxy, allyl and methallyl.

The (cycloalkyl)methyl group denoted by $R_1$ has 3 to 6 ring carbon atoms. Examples of such groups are: methylcyclopropyl, 3-methylcyclopentyl and 4-methylcyclohexyl. Preferred compounds because of their effectiveness are compounds of formula I wherein
$R_1$ represents methoxy or ethoxy,
$R_2$ represents methyl, ethyl, propyl, n-pentyl, n-hexyl, allyl or propargyl,
$R_3$ represents hydrogen,
$R_4$ and $R_5$ each represent methyl, ethyl or allyl,
X represents oxygen, and
Y represents sulphur, or
$R_4$ and $R_5$ form, with the nitrogen atom to which they are bound, the piperidino ring.

The compounds of formula I can be produced by the following methods known per se:

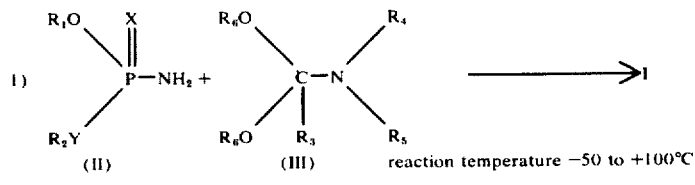

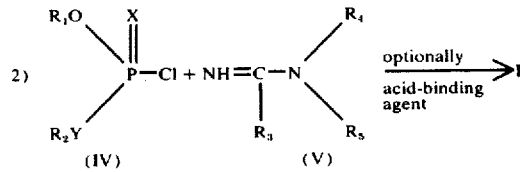

Conversion:

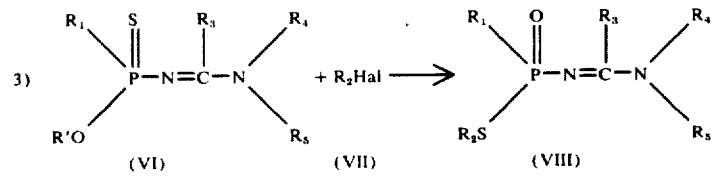

In formulae II to VIII, $R_1$ to $R_5$, X and Y have the meanings given for formula I, $R_6$ and R' stand for lower alkyl, and Hal for an anion, e.g. chlorine, bromine, iodine, or the radical of a sulphuric acid ester.

Suitable acid-binding agents are: tertiary amines, e.g. trialkylamines, pyridine, dialkylanilines; inorganic bases such as hydrides, hydroxides; carbonates and bicarbonates of alkali metals and alkaline-earth metals. The processes 1 and 2 are performed under normal pressure, with the exclusion of moisture, and in inert solvents or diluents.

Suitable inert solvents or diluents are, e.g. ethers and ethereal compounds such as diethyl ether, dipropyl ether, dioxane, tetrahydrofuran; aliphatic, aromatic as well as halogenated hydrocarbons, particularly benzene, toluene, xylenes, chloroform, chlorobenzene; and nitriles such as acetonitrile.

The starting materials of formulae II to V are in some cases known compounds which can be produced by known methods. Thus, the methods of production of the amide acetals required in the case of process 1 are described in 'Zeitschrift fur Chemie 9, 201 (1969)', and the production of (thio)phosphoric acid amides in 'Houben-Weyl, Methoden der organischen Chemie, Volume Phosphorus II'.

The compounds of formula I have a broad biocidal action and can be used for the control of the most diverse plant and animal pests.

The said compounds are particularly suitable for the control of insects of the families: Acrididae, Blattidae, Gryllidae, Gryllotalpidae, Tettigoniidae, Cimicidae, Phrrhocoridae, Reduviidae, Aphididae, Delphacidae, Diaspididae, Pseudococcidae, Chrysomelidae, Coccinellidae, Bruchidae, Scarabaeidae, Dermestidae, Tenebrionidae, Curculionidae, Tineidae, Noctuidae, Lymantriidae, Pyralidae, Galleriidae, Culicidae, Tipulidae, Stomoxydae, Muscidae, Calliphoridae, Trypetidae, Pulicidae, as well as acarides of the families: Ixodidae, Argasidae, Tetranychidae and Dermanyssidae.

The insecticidal or acaricidal action can be appreciably widened and adapted to suit given conditions by the addition of other insecticides and/or acaricides. Suitable additives are, for example, the following active substances:

ORGANIC PHOSPHORUS COMPOUNDS

Bis-0,0-diethylphosphoric acid anhydride (TEPP)
Dimethyl-(2,2,2-trichloro-1-hydroxyethyl)-phosphonate (TRICHLORFON)
1,2-dibromo-2,2-dichloroethyldimethylphosphate (NALED)
2,2-dichlorovinyldimethylphosphate (DICHLORVOS)
2-methoxycarbamyl-1-methylvinyldimethylphosphate (MEVINPHOS)
Dimethyl-1-methyl-2-(methylcarbamoyl)-vinylphosphate cis (MONOCROTOPHOS)
3-(dimethoxyphosphinyloxy)-N,N-dimethyl-ciscrotonamide (DICROTOPHOS)
2-chloro-2-diethylcarbamoyl-1-methylvinyldimethylphosphate (PHOSPHAMIDON)
0,0-diethyl-O(or S)-2-(ethylthio)-ethylthiophosphate (DEMETON) S-ethylthioethyl-0,0-dimethyl-dithiophosphate (THIOMETON)
0,0-diethyl-S-ethylmercaptomethyldithiophosphate (PHORATE)
0,0-diethyl-S-2-(ethylthio)ethyldithiophosphate (DISULFOTON)
0,0-dimethyl-S-2-(ethylsulphinyl)ethylthiophosphate (OXYDEMETON METHYL)
0,0-dimethyl-S-(1,2-dicarbethoxyethyldithiophosphate (MALATHION)
0,0,0,0-tetraethyl-S,S'-methylene-bis-dithiophosphate (ETHION)
O-ethyl-S,S-dipropyldithiophosphate
0,0-dimethyl-S-(N-methyl-N-formylcarbamoylmethyl)-dithiophosphate (FORMOTHION)
0,0-dimethyl-S-(N-methylcarbamoylmethyl)dithiophosphate (DIMETHOATE)
0,0-dimethyl-O-p-nitrophenylthiophosphate (PARATHION-METHYL)
0,0-diethyl-O-p-nitrophenylthiophosphate (PARATHION)
O-ethyl-O-p-nitrophenylphenylthiophosphate (EPN)
0,0-dimethyl-O-(4-nitro-m-tolyl)thiophosphate (FENITROTHION)
0,0-dimethyl-O-2,4,5-trichlorophenylthiophosphate (RONNEL)
O-ethyl-0,2,4,5-trichlorophenylethylthiophosphate (TRICHLORONATE)
0,0-dimethyl-O-2,5-dichloro-4-bromophenylthiophosphate (BROMOPHOS)
0,0-dimethyl-O-(2,5-dichloro-4-iodophenyl)-thiophosphate (JODOFENPHOS)
4-tert.butyl-2-chlorophenyl-N-methyl-O-methylamidophosphate (CRUFORMATE)
0,0-dimethyl-O-(3-methyl-4-methylmercaptophenyl)-thiophosphate (FENTHION)
Isopropylamino-O-ethyl-O-(4-methylmercapto-3-methylphenyl)phosphate
0,0-diethyl-O-p-(methylsulphinyl)phenyl-thiophosphate (FENSULFOTHION)
O-p-(dimethylsulphamido)phenyl-0,0-dimethylthiophosphate (FAMPHUR)
0,0,0',0'-tetramethyl-0,0'-thiodi-p-phenylenethiophosphate
O-ethyl-S-phenyl-ethyldithiophosphonate
0,0-dimethyl-O-(α-methylbenzyl-3-hydroxycrotonyl)-phosphate
2-chloro-1-(2,4-dichlorophenyl)vinyl-diethylphosphate (CHLORFENVINPHOS)
2-chloro-1-(2,4,5-trichlorophenyl)vinyl-dimethylphosphate
O-[2-chloro-1-(2,5-dichlorophenyl)]vinyl-0,0-diethylthiophosphate
Phenylglyoxylonitriloxime-0,0-diethylthiophosphate (PHOXIM)
0,0-diethyl-O-(3-chloro-4-methyl-2-oxo-2-H-1-benzopyran-7-yl)-thiophosphate (COUMAPHOS)
2,3-p-dioxandithiol-S,S-bis(0,0-diethyldithiophosphate) (DIOXATHION)
5-[(6-chloro-2-oxo-3-benzoxazolinyl)methyl]0,0-diethyldithiophosphate (PHOSALONE)
2-(diethoxyphosphinylimino)-1,3-dithiolane
0,0-dimethyl-S-[2-methoxy-1,3,4-thiadiazol-5-(4H)-onyl-(4)methyl]dithiophosphate
0,0-dimethyl-S-phthalimidomethyl-dithiophosphate (IMIDAN)
0,0-diethyl-O-(3,5,6-trichloro-2-pyridyl)thiophosphate
0,0-diethyl-O-2-pyrazinylthiophosphate (THIONAZIN)
0,0-diethyl-O-(2-isopropyl-4-methyl-6-pyrimidyl)thiophosphate (DIAZINON)
0,0-diethyl-O-(2-quinoxalyl)thiophosphate
0,0-dimethyl-S-(4-oxo-1,2,3-benzotriazin-3(4H)-ylmethyl)dithiophosphate (AZINPHOSMETHYL)
0,0-diethyl-S-(4-oxo-1,2,3-benzotriazin-3(4-H)-ylmethyl)dithiophosphate (AZINPHOSETHYL)
S-[(4,6-diamino-s-triazin-2-yl)methyl]-O,O-dimethyl-dithiophosphate (MENAZON)
O,O-dimethyl-0-(3-chloro-4-nirophenyl)thiophosphate (CHLORTHION)
0,0-dimethyl-0(or S)-2-(ethylthioetyl)tiophosphate (DEMETON-S-METHYL)
2-(0,0-dimethyl-phosphoryl-thiomethyl)-5-methoxypyrone-4-3,4-dichlorobenzyl-triphenylphosphonium-chloride
0,0-diethyl-S-(2,5-dichlorophenylthiomethyl)dithiophosphate (PHENKAPTON)
0,0-diethyl-0-(4-methyl-cumarinyl-7-)-thiophosphate (POTASAN)
5-amino-bis(dimethylamido)phosphinyl-3-phenyl-1,2,4-triazole (TRIAMIPHOS)
N-methyl-5-(0,0-dimethylthiolphosphoryl)-3-thiavaleramide (VAMIDOTHION)
0,0-diethyl-0-[2-dimethylamino-4-methylpyrimidyl-(6)]-thiophosphate (DIOCTHYL)

O,O-dimethyl-S-(methylcarbamoylmethyl)-thiophosphate (OMETHOATE)
O-ethyl-O-(8-quinolinyl)-phenylthiophosphonate (OXINOTHIOPHOS)
O-methyl-S-methyl-amidothiophosphate (MONITOR)
O-methyl-O-(2,5-dichloro-4-bromophenyl)-benzothiophosphate (PHOSVEL)
O,O,O,O-tetrapropyldithiophosphate
3-(dimethoxyphosphinyloxy)-N-methyl-N-methoxy-cis-crotonamide
O,O-dimethyl-S-(N-ethylcarbamoylmethyl)dithiophosphate (ETHOATE-METHYL)
O,O-diethyl-S-(N-isopropylcarbamoylmethyl)-dithiophosphate (PROTHOATE)
S-N-(1-cyano-1-methylethyl)carbamoylmethyldiethylthiolphosphate (CYANTHOATE)
S-(2-acetamidoethyl)-O,O-dimethyldithiophosphate
Hexamethylphosphoric acid triamide (HEMPA)
O,O-dimethyl-O-(2-chloro-4-nitrophenyl)thiophosphate (DICAPTHON)
O,O-dimethyl-O-p-cyanophenyl thiophosphate (CYANOX)
O-ethyl-O-p-cyanophenylthiophosphonate
O,O-diethyl-O,2,4-dichlorophenylthiophosphate (DICHLORFENTHION)
O,2,4-dichlorophenyl-O-methylisopropylamidothiophosphate
O,O-diethyl-O,2,5-dichloro-4-bromophenylthiophosphate (BROMOPHOS-ETHYL)
dimethyl-p-(methylthio)phenylphosphate
O,O-dimethyl-O-p-sulphamidophenylthiophosphate
O-[p-(p-chlorophenyl)azophenyl]O,O-dimethylthiophosphate AZOTHOATE)
O-ethyl-S-4-chlorophenyl-ethyldithiophosphonate
O-isobutyl-S-p-chlorophenyl-ethyldithiophosphate
O,O-dimethyl-S-p-chlorophenylthiophosphate
O,O-dimethyl-S-(p-chlorophenylthiomethyl)dithiophosphate
O,O-diethyl-p-chlorophenylmercaptomethyl-dithiophosphate CARBOPHENOTHION
O,O-diethyl-S-p-chlorophenylthiomethyl-thiophosphate
O,O-dimethyl-S-(carbethoxy-phenylmethyl)dithiophosphate (PHENTHOATE)
O,O-diethyl-S-(carbofluorethoxy-phenylmethyl)-dithiophosphate
O,O-dimethyl-S-carboisopropoxy-phenylmethyl)-dithiophosphate
O,O-diethyl-7-hydroxy-3,4-tetramethylene-coumarinyl-thiophosphate (COUMITHOATE)
2-methoxy-4-H-1,3,2,-benzodioxaphosphorin-2-sulphide
O,O-diethyl-O-(5-phenyl-3-isooxazolyl)thiophosphate
2-(diethoxyphosphinylimino)-4-methyl-1,3-dithiolane
tris-(2-methyl-1-aziridinyl)-phosphine oxide (METEPA)
S-(2-chloro-1-phthalimidoethyl)-O,O-diethyldithiophosphate
N-hydroxynaphthalimido-diethylphosphate
dimethyl-3,5,6-trichloro-2-pyridylphosphate
O,O-dimethyl-O-(3,5,6-trichloro-2-pyridyl)thiophosphate
S-2-(ethylsulphonyl)ethyl dimethylthiolphosphate -dioxydemeton-S-METHYL)
diethyl-S-2-(ethylsulphinyl)ethyl dithiophosphate (OXIDISULFOTON)
bis-O,O-diethylthiophosphoric acid anhydride (SULFOTEP)
dimethyl-1,3-di(carbomethoxy)-1-propen-2-yl-phosphate
dimethyl-(2,2,2-trichloro-1-butyroyloxyethyl)phosphate (BUTONATE)
O,O-dimethyl-O-(2,2-dichloro-1-methoxy-vinyl)phosphate bis-(dimethylamido)fluorphosphate (DIMEFOX)
3,4-dichlorobenzyl-triphenylphosphoniumchloride
dimethyl-N-methoxymethylcarbamoylmethyl-dithiophosphate (FORMOCARBAM)
O,O-diethyl-O-(2,2-dichloro-1-chloroethoxyvinyl)phosphate
O,O-dimethyl-O-(2,2-dichloro-1-chloroethoxyvinyl)-phosphate
O-ethyl-S,S-diphenyldithiolphosphate
O-ethyl-S-benzyl-phenyldithiophosphonate
O,O-diethyl-S-benzyl-thiolphosphate
O,O-dimethyl-S-(4-chlorophenylthiomethyl)dithiophosphate (METHYLCARBOPHENOTHION)
O,O-dimethyl-S-(ethylthiomethyl)dithiophosphate
diisopropylaminofluorophosphate (MIPAFOX)
O,O-dimethyl-S-(morpholinylcarbamoylmethyl)dithiophosphate (MORPHOTHION)
bismethylamido-phenylphosphate
O,O-dimethyl-S-(benzenesulphonyl)dithiophosphate
O,O-dimethyl-(S and O)-ethylsulphinylethylthiophosphate
O,O-diethyl-O-4-nitrophenylphosphate
triethoxy-isopropoxy-bis(thiophosphinyl)disulphide
2-methoxy-4H-1,3,2-benzodioxaphosphorin-2-oxide
octamethylpyrophosphoramide (SCHRADAN)
bis-(dimethoxythiophosphinylsulphido)-phenylmethane
N,N,N'N'-tetramethyldiamidofluorophosphate (DIMEFOX)
O-phenyl-O-p-nitrophenyl-methanethiophosphonate (COLEP)
O-methyl-O-(2-chloro-4-tert.butyl-phenyl)-N-methylamidothiophosphate (NARLENE)
O-ethyl-O-(2,4-dichlorophenyl)-phenylthiophosphonate
O,O-diethyl-O-(4-methylmercapto-3,5-dimethylphenyl)-thiophosphate
4,4'-bis-(O,O-dimethylthiophosphoryloxy)-diphenyl disulphide
O,O-di-(β-chloroethyl)-O-(3-chloro-4-methyl-coumarinyl-7)-phosphate
S-(1-phthalimidoethyl)-O,O-diethyldithiophosphate
O,O-dimethyl-O-(3-chloro-4-diethylsulphamylphenyl)-thiophosphate
O-methyl-O-(2-carbisopropoxyphenyl)-amidothiophosphate
5-(O,O-dimethylphosphoryl)-6-chloro-bicyclo(3.2.0)-heptadiene(1,5)
O-methyl-O-(2-i-propoxycarbonyl-1-methylvinyl)-ethylamidothiophosphate.

NITROPHENOLS AND DERIVATIVES 4,6-dinitro-6-methylphenol, sodium salt [Dinitrocresol]
dinitrobutylphenol-(2,2',2'')-triethanolamine salt
2-cyclohexyl-4,6-dinitrophenyl [Dinex]
2-(1-methylheptyl)-4,6-dinitrophenyl-crotonate [Dinocap]
2-sec.-butyl-4,6-dinitrophenyl-3-methyl-butenoate [Dinapacryl]
2-sec.-butyl-4,6-dinitrophenyl-cyclopropionate 2-sec.-butyl-4,6-dinitrophenylisopropylcarbonate [Dinobuton]

MISCELLANEOUS pyrethin I
pyrethin II
3-allyl-2-methyl-4-oxo-2-cyclopentan-1-yl-chrysanthemumate (Allethrin)
6-chloropiperonyl-chrysanthemumate (Barthrin)
2,4-dimethylbenzyl-chrysanthemumate (Dimethrin)
2,3,4,5-tetrahydrophthalimidomethylchrysanthemumate
4-chlorobenzyl-4-chlorophenylsulphide [Chlorobensid]
6-methyl-2-oxo-1,3-dithiolo-[4,5-b]-quinoxaline (Quinomethionate)
(I)-3-(2-furfuryl)-2-methyl-4-oxocyclopent-2-enyl(I)-(cis+trans)chrysanthemum-monocarboxylate [Furethrin]
2-pivaloyl-indane-1,3-dione [Pindon]
N'-(4-chloro-2-methylphenyl)-N,N-dimethylformamidine [Chlorophenamidin]
4-chlorobenzyl-4-fluorophenyl-sulphide [Fluorobenside]
5,6-dichloro-1-phenoxycarbamyl-2-trifluoromethyl-benzimidazole [Fenozaflor]
p-chlorophenyl-p-chlorobenzenesulphonate [Ovex]
p-chlorophenyl-benzenesulphonate [Fenson]
p-chlorophenyl-2,4,5-trichlorophenylsulphone [Tetradifon]
p-chlorophenyl-2,4,5-trichlorophenylsulphide [Tetrasul]
p-chlorobenzyl-p-chlorophenylsulphide [Chlorobenside]
2-thio-1,3-dithiolo-(5,6)-quinoxaline [Thiochinox]
prop-2-ynyl-(4-t-butylphenoxy)-cyclohexylsulphite [Propargil].

FORMAMIDINES 1-dimethyl-2-(2'-methyl-4'-chlorophenyl)-formamidine (CHLORPHENAMIDIN) 1-methyl-2-(2'-methyl-4'-chlorophenyl)-formamidine
1-methyl-2-(2'-methyl-4'-bromophenyl)-formamidine
1-methyl-2-(2',4'-dimethylphenyl)-formamidine
1-n-butyl-1-methyl-2-(2'-methyl-4'-chlorophenyl)-formamidine
1-methyl-1-(2'-methyl-4'-chloroaniline-methylene)-formamidine
2-(2''-methyl-4''-chlorophenyl-formamidine
1-n-butyl-2-(2'-methyl-4'-chlorophenyl-imino)-pyrolidine.

UREA

N-2-methyl-4-chlorophenyl-N',N'-dimethyl-thiourea.

CARBAMATES 1-naphthyl-N-methylcarbamate (CARBARYL)
2-butinyl-4-chlorophenylcarbamate
4-dimethylamino-3,5-xylyl-N-methylcarbamate
4-dimethylamino-3-tolyl-N-methylcarbamate (AMINOCARB)
4-methylthio-3,5-xylyl-N-methylcarbamate (METHIOCARB)
3,4,5-trimethylphenyl-N-methylcarbamate
2-chlorophenyl-N-methylcarbamate (CPMC)
5-chloro-6-oxo-2-norborane-carbonitrile-0-(methylcarbamoyl)-oxime
1-(dimethylcarbamoyl)-5-methyl-3-pyrazolyl-N,N-dimethylcarbamate (DIMETILAN)
2,3-dihydro-2,2-dimethyl-7-benzofuranyl-N-methylcarbamate (CARBOFURAN)
2-methyl-2-methylthio-propionaldehyde-0-(methylcarbamoyl)-oxime (ALDICARB)
8-quinaldyl-N-methylcarbamate and its salts
methyl-2-isopropyl-4-(methylcarbamoyloxy)carbanilate
m-(1-ethylpropyl)phenyl-N-methylcarbamate
3,5-di-tert.butyl-N-methylcarbamate
m-(1-methylbutyl)phenyl-N-methylcarbamate
2-isopropylphenyl-N-methylcarbamate
2-sec.butylphenyl-N-methylcarbamate
m-tolyl-N-methylcarbamate
2,3-xylyl-N-methylcarbamate
3-isopropylphenyl-N-methylcarbamate
3-tert.butylphenyl-N-methylcarbamate
3-sec.butylphenyl-N-methylcarbamate
3-isopropyl-5-methylphenyl-N-methylcarbamate (PROMECARB)
3,5-diisopropylphenyl-N-methylcarbamate
2-chloro-5-isopropylphenyl-N-methylcarbamate
2-chloro-4,5-dimethylphenyl-N-methylcarbamate
2-(1,3-dioxolan-2-yl)phenyl-N-methylcarbamate (DIOXACARB)
2-(4,5-dimethyl-1,3-dioxolan-2-yl)phenyl-N-methylcarbamate
2-(1,3-dioxolan-2-yl)phenyl-N,N-dimethylcarbamate
2-(1,3-dithiolan-2-yl)-N,N-dimethylcarbamate
2-(1,3-dithiolan-2-yl)phenyl-N,N-dimethylcarbamate
2-isopropoxyphenyl-N-methylcarbamate (APROCARB)
2-(2-propinyloxy)phenyl-N-methylcarbamate
3-(2-propinyloxy)phenyl-N-methylcarbamate
2-dimethylcaminophenyl-N-methylcarbamate
2-diallylaminophenyl-N-methylcarbamate
4-diallyamino-3,5-xylyl-N-methylcarbamate (ALLYXICARB)
4-benzothienyl-N-methylcarbamate
2,3-dihydro-2-methyl-7-benzofuranyl-N-methylcarbamate
3-methyl-1-phenylpyrazol-5-yl-N,N-dimethylcarbamate
1-isopropyl-3-methylpyrazol-5-yl-N,N-dimethylcarbamate (ISOLAN)
2-dimethylamino-5,6-dimethylpyrimidin-4-yl-N,N-dimethyl-carbamate
3-methyl-4-dimethylaminomethyleneiminophenyl-N-methylcarbamate
3,4-dimethylphenyl-N-methylcarbamate
2-cyclopentylphenyl-N-methylcarbamate
3-dimethylamino-methyleneiminophenyl-N-methylcarbamate (FORMETANATE) and its salts
1-methylthio-ethylimino-N-methylcarbamate (METHOMYL)
2-methylcarbamoyloximino-1,3-dithiolane
5-methyl-2-methylcarbamoyloximino-1,3-oxythiolane
2-(1-methoxy-2-propoxy)phenyl-N-methylcarbamate
2-(1-butin-3-yl-oxy)phenyl-N-methylcarbamate
1-dimethylcarbamyl-1-methylthio-0-methylcarbamyl-formoxime
1-(2'-cyanoethylthio)-0-methylcarbamyl-acetaldoxime
1-methylthio-0-carbamyl-acetaldoxime
0-(3-sec.butylphenyl)-N-phenylthio-N-methylcarbamate
2,5-dimethyl-1,3-dithiolane-2-(0-methylcarbamyl)-aldoxime)

0-2-diphenyl-N-methylcarbamate
2-(N-methylcarbamyl-oximino)-3-chloro-bicyclo[2.2.1]heptane
2-(N-methylcarbamyl-oximino)-bicyclo[2.2.1]heptane
3-isopropylphenyl-N-methyl-N-chloroacetal-carbamate
3-isopropylphenyl-N-methyl-N-methylthiomethyl-carbamate
0-(2,2-dimethyl-4-chloro-2,3-dihydro-7-benzofuranyl)-N-methylcarbamate
0-(2,2,4-trimethyl-2,3-dihydro-7-benzofuranyl)-N-methylcarbamate
0-naphthyl-N-methyl-N-acetal-carbamate
0-5,6,7,8-tetrahydronaphthyl-N-methyl-carbamate
3-isopropyl-4-methylthio-phenyl-N-methylcarbamate
3,5-dimethyl-4-methoxy-phenyl-N-methylcarbamate
3-methoxymethoxy-phenyl-N-methylcarbamate
3-allyloxyphenyl-N-methylcarbamate
2-propargyloxymethoxy-phenyl-N-methyl-carbamate
2-allyloxyphenyl-N-methyl-carbamate
4-methoxycarbonylamino-3-isopropylphenyl-N-methyl-carbamate
3,5-dimethyl-4-methoxycarbonylamino-phenyl-N-methyl-carbamate
2-γ-methylthiopropylphenyl-N-methyl-carbamate
3-(α-methoxymethyl-2-propenyl)-phenyl-N-methyl-carbamate
2-chloro-5-tert.-butyl-phenyl-N-methyl-carbamate
4-(methyl-propargylamino-3,5-xylyl-N-methyl-carbamate
4-(methyl-γ-chloroallylamino)-3,5-xylyl-N-methyl-carbamate
4-(methyl-β-chloroallylamino)-3,5-xylyl-N-methyl-carbamate
1-(β-ethoxycarbonylethyl)-3-methyl-5-pyrazolyl-N,N-dimethylcarbamate
3-methyl-4-(dimethylamino-methylmercapto-methyleneimino)phenyl-N-methylcarbamate
1,3-bis(carbamoylthio)-2-(N,N-dimethylamino)-propanehydrochloride
5,5-dimethylhydroresorcinoldimethylcarbamate
2-[ethyl-propargylamino]-phenyl-N-methylcarbamate
2-[methyl-propargylamino]-phenyl-N-methylcarbamate
4-[dipropargylamino]-3-tolyl-N-methylcarbamate
4-[dipropargylamino]-3,5-xylyl-N-methylcarbamate
2-[ailyl-isopropylamino]-phenyl-N-methylcarbamate
3-[allyl-isopropylamino]-phenyl-N-methylcarbamate

CHLORINATED HYDROCARBONS

γ-hexachlorocyclohexane [GAMMEXANE; LINDAN; γ HCH]
1,2,4,5,6,7,8,8-octachloro-3α,4,7,7α'tetrahydro-4,7-methylene indane [CHLORDAN]
1,4,5,6,7,8,8-heptachloro,3α,4,7,7α-tetrahydro-4,7-methylene indane [heptachlor]
1,2,3,4,10,10-hexachloro-1,4,4α,5,8,8α-hexahydro-endo-1,4-exo-5,8-dimethanonaphthalene [ALDRIN]
1,2,3,4,10,10-hexachloro-6,7-epoxy-1,4,4α,5,6,7,8,8α-octahydro-exo-1,4-endo-5,8-dimethanonaphthalene [DIFLORIN]
1,2,3,4,10,10-hexachloro-5,7-epoxy-1,4,4α,5,6,7,8,8α-octyhydro-endo-endo-5,8-dimethanonaphthalene [ENDRIN].

In addition to possessing the above mentioned properties, the compounds of formula I are moreover effective against members of the division *Thallophyta*. Some of these compounds thus have a bactericidal action. They are, however, particularly effective against fungi, especially against the phytopathogenic fungi belonging to the following classes: Oomycetes, Zygomycetes, Ascomycetes, Basidiomycetes, Denteromycetes. The compounds of formula I also have a fungitoxic action in the case of fungi which attack the plants from the soil. Furthermore, the new active substances are suitable for the treatment of seed, fruit, tubers, etc., for protection against fungus infections. The compounds of formula I are suitable too for the control of phytopathological nematodes.

The compounds of formula I can be used on their own or together with suitable carriers and/or additives. Suitable carriers and additives may be solid or liquid, and correspond to the substances common in formulation practice, such as, e.g. natural and regenerated substances, solvents, dispersing agents, wetting agents, adhesives, thickeners, binders and/or fertilizers.

For application, the compounds of formula I can be processed into the form of dusts, emulsion concentrates, granulates, dispersions, sprays, or solutions, the formulation of these preparations being effected in a manner commonly known in practice. Also to be mentioned are cattle dips and spray races, in which aqueous preparations are used.

The agents according to the invention are produced in a manner known per se by the intimate mixing and/or grinding of active substances of formula I with the suitable carriers, optionally with the addition of dispersing agents or solvents which are inert to the active substances. The active substances can be obtained and used in the following preparation forms:

solid preparations: dusts, scattering agents, granulates, coated granulates, impregnated granulates and homogeneous granulates;

liquid preparations:
  a. water dispersible active substance concentrates: wettable powders, pastes, emulsions;
  b. solutions.

The solid preparations (dusts, scattering agents) are produced by the mixing of the active substances with solid carriers. Suitable carriers are, e.g. kaolin, talcum, bole, loess, chalk, limestone, ground limestone, attapulgite, dolomite, diatomaceous earth, precipitated silicic acid, alkaline-earth silicates, sodium and potassium aluminum silicates (feldspar and mica), calcium and magnesium sulphates, magnesium oxide, ground synthetic materials, fertilizers such as ammonium sulphate, ammonium phosphate, ammonium nitrate, urea, ground vegetable products such as bran, bark dust, sawdust, ground nutshells, cellulose powder, residues of plant extractions, active charcoal, etc., alone or in admixture with each other.

Granulates can be very easily prepared by a process in which an active substance of formula I is dissolved in an organic solvent, the thus obtained solution applied to a granulated mineral, e.g. attapulgite, $SiO_2$, granicalcium, bentonite, etc., and the organic solvent then evaporated off.

It is possible also to produce polymer granulates; in this case the active substances of formula I are mixed with polymerisable compounds (urea/formaldehyde; dicyandiamide/formaldehyde; melamine/formaldehyde, or others); polymerisation is then carefully carried out in a manner which leaves the active substances unaffected, and granulation performed actually during the gel forming process. It is more favourable, however, to impregnate finished porous polymer granules (urea/-formaldehyde, polyacrylonitrile, polyester and others), having a specific surface area and a favourable predeterminable adsorption/desorption ratio, with the active substances, e.g. in the form of their solutions (in a low-boiling solvent), and to then remove the solvent. Polymer granulates of this kind can be also sprayed in the form of microgranulates, having bulk weights of preferably 300 g/liter to 600 g/liter, with the aid of spray apparatus. Spraying can be carried out over extensive areas of useful plant crops by the use of aeoplanes.

Granulates can also be obtained by the compacting of the carrier material with the active substances and additives, and a subsequent reducing operation.

Moreover, it is possible to add to these mixtures additives stabilizing the active substance and/or non-ionic, anion-active and cation-active substances which improve, e.g. the adhesiveness of the active substances on plants and parts of plants (adhesives and agglutinants), and/or ensure a better wettability (wetting agents) as well as dispersibility (dispersing agents).

The following substances are, for example, suitable: olein/lime mixture, cellulose derivatives (methyl cellulose, carboxymethyl cellulose), hydroxyethylene glycol ethers of monoalkyl and dialkyl phenols having 5 to 15 ethylene oxide radicals per molecule and 8 to 9 carbon atoms in the alkyl radical, ligninsulphonic acid, the alkali metal and alkaline-earth metal salts thereof, polyethylene glycol ethers (carbowaves), fatty alcohol polyglycol ethers having 5 to 20 ethylene oxide radicals per molecule and 8 to 18 carbon atoms in the fatty alcohol moiety, condensation products of ethylene oxide, propylene oxide, polyvinylpyrrolidones, polyvinyl alcohols, condensation products of urea and formaldehyde, as well as latex products.

Water-dispersible concentrates of active substances, i.e. wettable powders, pastes and emulsion concentrates, are agents which can be diluted with water to obtain any desired concentration. They consist of active substance, carrier, optionally additives which stabilise the active substance, surface-active substances, and anti-foam agents and, optionally, solvents.

The wettable powders and pastes are obtained by the mixing and grinding of the active substances with dispersing agents and pulverulent carriers, in suitable devices, until homogeneity is obtained. Suitable carriers are, e.g. those previously mentioned in the case of solid preparations. It is advantageous in some cases to use mixtures of different carriers. As dispersing agents it is possible to use, e.g.: condensation products of sulphonated naphthalene and sulphonated naphthalene derivatives with formaldehyde, condensation products of napthalene or of naphthalenesulphonic acids with phenol and formaldehyde, as well as alkali, ammonium and alkaline-earth metal salts of ligninsulphonic acid, also alkylarylsulphonates, alkali metal salts and alkaline-earth metal salts of dibutyl naphthalenesulphonic acid, fatty alcohol sulphates such as salts of sulphated hexadecanols, heptadecanols, octadecanols, and salts of sulphated fatty alcohol glycol ethers, the sodium salt of oleyl methyl tauride, ditertiary ethylene glycols, dialkyl dilauryl ammonium chloride, and fatty acid alkali-metal and alkaline-earth metal salts.

Suitable anti-foam agents are, e.g. silicon oils.

The active substances are so mixed, ground, sieved and strained with the above mentioned additives that the solid constituent in the case of wettable powders has a particle size not exceeding 0.02 to 0.04 mm, and in the case of pastes not exceeding 0.03 mm. For the preparation of emulsion concentrates and pastes, dispersing agents are used such as those mentioned in the preceding paragraphs, organic solvents and water. Suitable solvents are, e.g. alcohols, benzene, xylene, toluene, dimethylsulphoxide, and mineral oil fractions boiling in the range of 120° to 350°C. The solvents must be practically odourless and inert to the active substances.

Furthermore, the agents according to the invention can be used in the form of solutions. For this purpose, the active substance, or several active substances, of the general formula I is dissolved in suitable organic solvents, solvent mixtures, or water. As organic solvents it is possible to use aliphatic and aromatic hydrocarbons, their chlorinated derivatives, alkylnaphthalenes, mineral oils on their own or in admixture with each other.

The content of active substance in the above described agents is between 0.1 and 95%; it is to be mentioned in this connection that in the case of application of the agents from an aeroplane, or by means of some other suitable application devices, concentrations of up to 99.5% can be used, or even the pure active substance.

The active substances of formula I can be prepared, e.g. as follows:

Dusts:

The following substances are used for the preparation of a) a 5% dust, and b) a 2% dust:

a) 5 parts of active substance
   95 parts of talcum.
b) 2 parts of active substance
   1 part of highly dispersed silicic acid
   97 parts of talcum.

The active substances are mixed and ground with the carriers.

Granulate:

The following substances are used to produce a 5 % granulate:

5 parts of active substance,
0.25 parts of epichlorhydrin,
0.25 parts of cetyl polyglycol ether,
3.50 parts of polyethylene glycol,
91 parts of kaolin (particle size 0.3–0.8 mm).

The active substance is mixed with epichlorhydrin and dissolved with 6 parts of acetone; the polyethylene glycol and cetyl polyglycol ether are then added. The thus obtained solution is sprayed on to kaolin, and the acetone subsequently evaporated in vacuo.

Wettable powder:

The following constituents are used for the preparation of (a) a 40%, (b) and (c) a 25%, and (d) a 10% wettable powder:

a) 40 parts of active substance,
   5 parts of sodium lignin sulphonate,
   1 part of sodium dibutyl-naphthalene sulphonate,
   54 parts of silicic acid.
b) 25 parts of active substance,
   4.5 parts of calcium lignin sulphonate
   1.9 parts of Champagne chalk/hydroxyethyl cellulose mixture (1:1),
   1.5 parts of sodium dibutyl naphthalene sulphonate,
   19.5 parts of silicic acid,
   19.5 parts of Champagne chalk,
   28.1 part of kaolin.
c) 25 parts of active substance,
   2.5 parts of isooctylphenoxy-polyoxyethylene-ethanol,
   1.7 parts of Champagne chalk/hydroxyethyl -continued

| | cellulose mixture (1:1), |
|---|---|
| 8.3 | parts of sodium aluminium silicate, |
| 16.5 | parts of kieselguhr, |
| 46 | parts of kaolin. |
| d) 10 | parts of active substance, |
| 3 | parts of a mixture of the sodium salts of saturated fatty alcohol sulphates, |
| 5 | parts of naphthalenesulphonic acid/formaldehyde condensate, |
| 82 | parts of kaolin. |

The active substances are intimately mixed, in suitable mixers, with the additives, the mixture being then ground in the appropriate mills and rollers. Wettable powders are obtained which can be diluted with water to give suspensions of any desired concentration.

Emulsifiable concentrates:

The following substances are used to produce (a) a 10% and (b) a 25% emulsifiable concentrate:

| a) | 10 | parts of active substance, |
|---|---|---|
| | 3.4 | parts of epoxidised vegetable oil, |
| | 13.4 | parts of a combination emulsifier consisting of fatty alcohol polyglycol ether and alkylarylsulphonate calcium salt, |
| | 40 | parts of dimethylformamide, |
| | 43.2 | parts of xylene. |
| b) | 25 | parts of active substance, |
| | 2.5 | parts of epoxidised vegetable oil, |
| | 10 | parts of an alkylarylsulphonate/fatty alcoholpolyglycol ether mixture |
| | 5 | parts of dimethylformamide, |
| | 57.5 | parts of xylene. |

From these concentrates it is possible to produce, by dilution with water, emulsions of any desired concentration.

Spray:

The following constituents are used to prepare a 5% spray:

5 parts of active substance,
1 part of epichlorhydrin,
94 parts of ligroin (boiling limits 160°–190°C).

EXAMPLE 1 a.

N,N-dimethyl-N'-0,0-dimethyl-thiophosphinyl-formamidine

A mixture of 14.1 g of thiophosphoric acid-0,0-dimethyl ester and 13 g of dimethylformamide-dimethylacetal is heated for one hour at 50°–60°C. The formed methanol and the excess of acetal are distilled off under 15–20 Torr, and an amount of 19.5 g of the compound of the formula

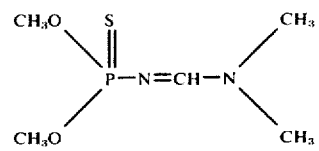

obtained as oil having a refraction of $n_D^{25} = 1.5275$.
NMR-spectrum:
doublet at 6.3 + 6.75 CPS (=CH—);
doublet at 3.6 + 3.8 CPS (CH$_3$O—);
doublet at 3.1 + 3.25 CPS (CH$_3$—N=);
intensity 1 : 6 : 6 b.

N,N-dimethyl-N'-0,0-dimethyl-thiophosphinyl-acetamidine

An amount of 17.1 g of thiophosphoric acid-0,0-dimethyl ester chloride is added dropwise at -5° to +50°C to a solution of 8.6 g of N,N-dimethyl-acetamidine and 10.1 g of triethylamine in 200 ml of dimethyl ether. Stirring is performed for 10 hours at room temperature and for 2 hours under reflux; the precipitated trimethylamine hydrochloride is then separated by filtration. After the ether has been distilled off there is obtained 20.8 g of the compound of the formula

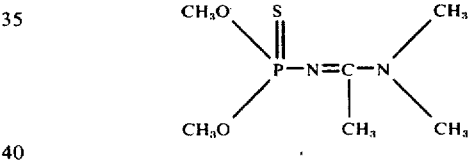

as a crystalline base.

A sample recrystallised from methanol metls at 48°–49°C.

Further compounds obtained in an analogous manner are as follows:

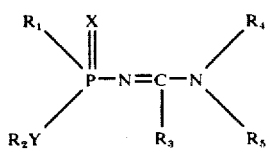

| R$_1$ | R$_2$ | R$_3$ | R$_4$ | R$_5$ | X | Y | Physical data |
|---|---|---|---|---|---|---|---|
| CH$_3$O | CH$_3$ | H | CH$_3$ | CH$_3$ | O | S | |
| CH$_3$O | CH$_3$ | H | CH$_3$ | —CH$_2$—⟨furfuryl⟩ | S | O | $n_D^{25}$ = 1,5278 |
| CH$_3$O | CH$_3$ | H | CH$_3$ | —CH$_2$—⟨tetrahydrofurfuryl⟩ | S | O | $n_D^{25}$ = 1,5252 |
| CH$_3$O | CH$_3$ | H | CH$_3$ | —CH$_2$—⟨furyl⟩ | S | O | $n_D^{25}$ = 1,5409 |
| CH$_3$O | CH$_3$ | CH$_3$ | CH$_3$ | CH$_3$ | O | S | $n_D^{25}$ = 1,5149 |
| CH$_3$O | CH$_3$ | H | —CH$_2$—CH$_2$—O—CH$_2$—CH$_2$— | | O | S | |

-continued

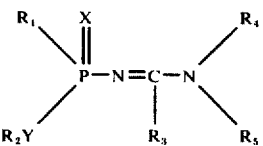

| R₁ | R₂ | R₃ | R₄ | R₅ | X | Y | Physical data |
|---|---|---|---|---|---|---|---|
| CH₃O | CH₃ | H | —CH₂—CH₂—O—CH₂—CH₂— | | S | O | $n_D^{25} = 1.5341$ |
| CH₃O | CH₃ | H | CH₃ | CH₃ | O | O | $n_D^{20} = 1.4757$ |
| C₂H₅O | (n)C₃H₇ | H | CH₃ | CH₃ | O | S | $n_D^{20} = 1.5085$ |
| C₂H₅O | C₂H₅ | H | CH₃ | CH₃ | O | S | $n_D^{25} = 1.5138$ |
| C₂H₅O | CH₃ | H | CH₃ | CH₃ | O | S | $n_D^{25} = 1.5247$ |
| CH₃O | CH₃ | H | —CH₂—CH₂—CH₂—CH₂—CH₂— | | O | S | $n_D^{20} = 1.5445$ |
| C₂H₅O | (n)C₃H₇ | H | —CH₂—CH₂—CH₂—CH₂—CH₂— | | O | S | $n_D^{25} = 1.5225$ |
| CH₃O | CH₃ | H | —CH₂—CH₂—CH₂—CH₂—CH₂— | | O | O | $n_D^{20} = 1.4971$ |
| C₂H₅O | C₂H₅ | H | CH₃ | CH₃ | S | O | $n_D^{25} = 1.5275$ |
| C₂H₅O | CH₂=CH—CH₂— | H | CH₃ | CH₃ | O | S | |
| C₂H₅O | (n)C₃H₇ | H | C₂H₅ | C₂H₅ | O | S | $n_D^{25} = 1.5002$ |
| CH₃O | CH₃ | H | C₂H₅ | C₂H₅ | O | S | |
| CH₃O | CH₃ | H | C₂H₅ | C₂H₅ | O | O | $n_D^{25} = 1.4649$ |
| C₂H₅O | CH₃ | H | —CH₂—CH₂—O—CH₂—CH₂— | | O | S | $n_D^{25} = 1.5269$ |
| C₂H₅O | C₂H₅ | H | C₂H₅ | C₂H₅ | S | O | $n_D^{25} = 1.4989$ |
| C₂H₅O | C₂H₅ | H | CH₃ | CH₃ | S | O | |
| C₂H₅O | C₂H₅ | H | —CH₂—CH₂—O—CH₂—CH₂— | | S | O | $n_D^{25} = 1.5143$ |
| CH₃O | C₂H₅ | H | CH₃ | CH₃ | O | S | $n_D^{25} = 1.5384$ |
| CH₃O | (n)C₃H₇ | H | CH₃ | CH₃ | O | S | |
| CH₃O | CH₂=CH—CH₂— | H | CH₃ | CH₃ | O | S | $n_D^{25} = 1.5379$ |
| CH₃O | CH≡C—CH₂— | H | CH₃ | CH₃ | O | S | |
| C₂H₅O | CH₃ | H | —CH₂—CH₂—O—CH₂—CH₂— | | O | S | |
| C₂H₅O | (n)C₃H₇ | H | —CH₂—CH₂—O—CH₂—CH₂— | | O | S | |
| C₂H₅O | CH₂=CH—CH₂— | H | —CH₂—CH₂—O—CH₂—CH₂— | | O | S | |
| CH₃O | CH₃ | H | —CH₂—CH=CH₂—CH₂—CH=CH₂ | | S | O | $n_D^{25} = 1.5187$ |
| CH₃O | C₂H₅ | H | —CH₂—CH=CH₂—CH₂—CH=CH₂ | | O | S | $n_D^{25} = 1.5229$ |
| CH₃O | (n)C₃H₇ | H | —CH₂—CH=CH₂—CH₂—CH=CH₂ | | O | S | $n_D^{25} = 1.5221$ |
| CH₃O | CH=C—CH₂— | H | —CH₂—CH=CH₂—CH₂—CH=CH₂ | | O | S | $n_D^{25} = 1.5438$ |
| CH₃O | CH≡C—CH₂— | H | —CH₂—CH=CH₂—CH₂—CH=CH₂ | | O | S | |
| CH₃O | (n)C₆H₁₃ | H | —CH₂—CH=CH₂—CH₂—CH=CH₂ | | O | S | $n_D^{25} = 1.5191$ |
| CH₃O | CH₃ | H | —CH₂—CH₂—CH₂—CH₂—CH₂— | | S | O | M.P. = 35°C |
| CH₃O | C₂H₅ | H | —CH₂—CH₂—CH₂—CH₂—CH₂— | | O | S | |
| CH₃O | (n)C₃H₇ | H | —CH₂—CH₂—CH₂—CH₂—CH₂— | | O | S | |
| CH₃O | CH₂=CH—CH₂— | H | —CH₂—CH₂—CH₂—CH₂—CH₂— | | O | S | |
| CH₃O | CH≡C—CH₂— | H | —CH₂—CH₂—CH₂—CH₂—CH₂— | | O | S | |
| CH₃O | (n)C₇H₁₅ | H | —CH₂—CH₂—CH₂—CH₂—CH₂— | | O | S | $n_D^{25} = 1.5406$ |
| C₂H₅O | (n)C₃H₇ | H | CH₃ | CH₃ | S | S | $n_D^{23} = 1.5488$ |
| C₂H₅ | C₂H₅ | H | CH₃ | CH₃ | O | S | $n_D^{23} = 1.5288$ |
| C₂H₅ | C₂H₅ | H | CH₃ | CH₃ | S | O | $n_D^{23} = 1.5262$ |
| C₂H₅ | C₂H₅ | H | C₂H₅ | C₂H₅ | S | O | $n_D^{23} = 1.5018$ |
| C₂H₅ | C₂H₅ | H | C₂H₅ | C₂H₅ | O | S | |
| C₂H₅O | C₂H₅ | H | CH₃ | CH₃ | S | S | |

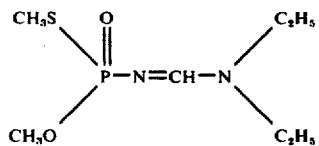

EXAMPLE 2

A. Insecticidal stomach poison action

Cotton plants were sprayed with a 0.05% aqueous active substance emulsion (obtained from a 10% emulsifiable concentrate).

After the drying of the coating, Spodoptera litoralis or Heliothis virescens larvae (L₃) were placed on each of the cotton plants. The test was carried out at 24°C with 60° relative humidity.

The compounds according to Example 1 exhibited in the above test a good stomach poison action against Spodoptera and Heliothis larvae.

B. Systemic insecticidal action

In order to determine the systemic action, rooted bean plants (Vicia faba) were placed into a 0.01% aqueous active substance solution (obtained from a 10% emulsifiable concentrate). After a period of 24 hours, bean aphids (Aphis fabae) were placed onto the parts of the plants above the soil. The insects were protected by a special device from the effect of contact and of gas. The test was carried out at 24°C with 70% relative humidity.

In the above tests, the compounds according to Example 1 exhibited stomach poison action and systemic insecticidal action.

EXAMPLE 3

Action against Chilo suppressalis

Rice plants of the type Caloro were planted, 6 plants per pot, in plastic pots having a top diameter of 17 cm, and grown to a height of ca. 60 cm. Infestation with Chilo suppressalis larvae (L₁; 3–4 mm long) was carried out 2 days after application of the active substance in granular form (amount applied 8 kg of active substance per hectare) to the paddy water. The evaluation of the insecticidal action was made 10 days after application of the granules.

The compounds according to Example 1 were effective against Chilo suppressalis in the above test.

EXAMPLE 4

Action against ticks

A. *Rhipicephalus bursa*

In each case, 5 adult ticks or 50 tick larvae were placed into a small glass test tube; the test tubes were then immersed for 1 to 2 minutes in 2 ml of an aqueous emulsion from a dilution series of 100, 10, 1 and 0.1 ppm of test substance. The tubes were then sealed with a standardised cotton plug, and inverted so that the active substance emulsion could be absorbed by the cotton wool.

An evaluation in the case of the adults was made after 2 weeks, and in the case of the larvae after 2 days. There were two repeats for each test.

B. *Boophilus microplus* (larvae)

With a dilution series analogous to that in Test A, tests were carried out using in each case 20 sensitive larvae and OP-resistant larvae, respectively (the resistance is with respect to diazinon compatibility).

The compounds according to Example 1 were effective in these tests against adults and larvae of Rhipicephalus bursa and against sensitive and OP-resistant larvae, respectively, of Boophilus microplus.

EXAMPLE 5

*Acaricidal action*

Phaseolus vulgaris (plants) were infested, 12 hours before the test for acaricidal action, by means of an infested piece of leaf from a mass culture of Tetranychus urticae. The transferred mobile stages were sprayed with the emulsified test preparations from a chromatography-sprayer in a manner ensuring no running off of the spray liquor. As assessment was made 2 to 7 days, by examination under a binocular, of living and of dead larvae, adults and eggs, and the results expressed in percentages. The treated plants were kept during the "holding time" in greenhouse compartments at 25°C.

The compounds according to Example 1 were effective in the above test against adults, larvae and eggs of Tetranychus urticae.

EXAMPLE 6

Action against soil nematodes

In order to test the action against soil nematodes the active substances were added, in the concentration stated in each case, to soil infested with root-gall-nematodes (Meloidogyne arenaria), and the whole intimately mixed. In the one test series, tomato seedlings were planted immediately afterwards in the thus prepared soil, and in the other test series tomatoes were planted after a waiting time of 8 days.

For an assessment of the nematicidal action, the galls present on the roots were counted 28 days after the planting and sowing, respectively.

The active substances according to Example 1 exhibited in this test a good action against Meloidogyne arenaria.

I claim:

1. A method for combatting insects or acarids which comprises applying thereto an insecticidally or acaricidally effective amount of a compound of the formula

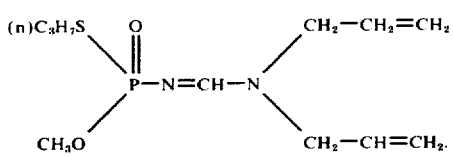

2. A method for combatting insects or acarids which comprises applying thereto an insecticidally or acaricidally effective amount of a compound of the formula

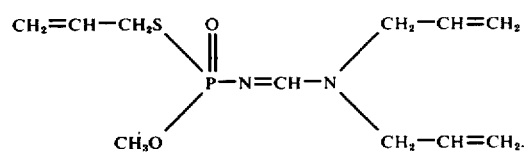

3. A method for combatting insects or acarids which comprises applying thereto an insecticidally or acaricidally effective amount of a compound of the formula

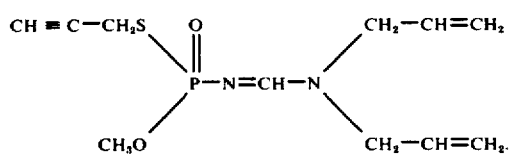

4. A method for combatting insects or acarids which comprises applying thereto an insecticidally or acaricidally effective amount of a compound of the formula

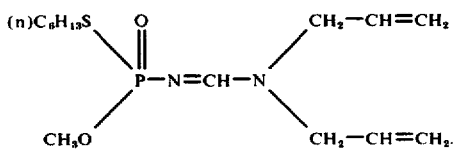

5. A method for combatting insects or acarids which comprises applying thereto an-insecticidally or acaricidally effective amount of a compound of the formula

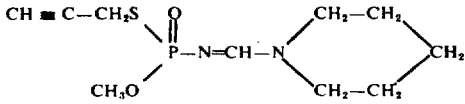

* * * * *